United States Patent
Boiten

(10) Patent No.: US 7,963,998 B2
(45) Date of Patent: Jun. 21, 2011

(54) HIP JOINT PROSTHESIS

(75) Inventor: Herman Boiten, Gottingen (DE)

(73) Assignee: Otto Bock Healthcare GmbH, Duderstadt (DE)

( * ) Notice: Subject to any disclaimer, the term of this patent is extended or adjusted under 35 U.S.C. 154(b) by 251 days.

(21) Appl. No.: 12/280,847

(22) PCT Filed: Feb. 22, 2007

(86) PCT No.: PCT/DE2007/000351
§ 371 (c)(1),
(2), (4) Date: Aug. 27, 2008

(87) PCT Pub. No.: WO2007/095933
PCT Pub. Date: Aug. 30, 2007

(65) Prior Publication Data
US 2009/0192625 A1      Jul. 30, 2009

(30) Foreign Application Priority Data
Feb. 27, 2006   (DE) .......................... 10 2006 009 510

(51) Int. Cl.
*A61F 2/64* (2006.01)
(52) U.S. Cl. ................................ 623/44; 623/43; 623/45
(58) Field of Classification Search ............... 623/22.11, 623/26, 30, 31, 43, 44, 45; 188/266
See application file for complete search history.

(56) References Cited

U.S. PATENT DOCUMENTS

| | | | |
|---|---|---|---|
| 3,090,964 A | 5/1963 | McLaurin |
| 4,051,558 A | 10/1977 | Vallotton |
| 4,215,441 A | 8/1980 | Wilson |
| 5,746,774 A | 5/1998 | Kramer et al. |
| 5,904,721 A | 5/1999 | Henry et al. |
| 6,322,594 B1 | 11/2001 | Boiten et al. |
| 6,558,430 B1 | 5/2003 | Nakaya et al. |

FOREIGN PATENT DOCUMENTS

| | | |
|---|---|---|
| CA | 2134999 | 5/1995 |
| DE | 9320853 | 3/1995 |
| DE | 19621034 | 12/1996 |
| DE | 19935203 | 1/2001 |
| DE | 60015384 | 10/2005 |
| JP | 53-4395 | 6/1977 |
| JP | 07-250852 | 10/1995 |
| JP | 2001137268 | 5/2001 |
| WO | 0117466 | 3/2001 |

OTHER PUBLICATIONS

International Search Report for PCT/DE2007/000351, mailed Sep. 27, 2007, 5 pages.

*Primary Examiner* — Corrine M McDermott
*Assistant Examiner* — Matthew Schall
(74) *Attorney, Agent, or Firm* — Holland & Hart, LLP

(57) ABSTRACT

A hip joint prosthesis includes connection means for securing the hip joint prosthesis to a securing device and to an artificial leg, and a control unit for controlling an extension movement in the hip joint and for controlling the step length of the artificial leg.

18 Claims, 9 Drawing Sheets

HIP JOINT PROSTHESIS

CROSS-REFERENCE TO RELATED APPLICATION

This application is a national stage application, filed pursuant to 35 U.S.C. §371, of PCT/DE2007/000351 filed Feb. 22, 2007, which claims priority to DE 10 2006 009 510.3 filed Feb. 27, 2006, both of which are herein incorporated by reference in their entirety.

TECHNICAL FIELD

The invention relates to a hip joint prosthesis for an artificial leg, with connection means for securing the hip joint prosthesis to an upper securing device, and with an artificial leg connected to the hip joint prosthesis. The invention can be used in particular in cases of disarticulation of the hip joint.

BACKGROUND

Walking with a hip joint prosthesis, particularly with an artificial leg secured to it, is difficult because three joints, namely the hip joint, the knee joint and the ankle joint have to be controlled without the prosthesis wearer being able to actively influence these joints. In particular, control of the movements of the hip joint is important for locomotion and for stability in the stance phase.

To ensure that the hip joint extends after a heel strike, the joint axes in conventional hip joint prostheses are arranged anterior to the joint axes of a natural hip joint. This concept is described in U.S. Pat. No. 3,090,964 A1, in which the proposed arrangement ensures that a maximum extension of the hip joint is adopted shortly after the heel strike.

U.S. Pat. No. 4,215,441 describes a leg prosthesis secured to a pelvic basket and having a spring which, during the stance phase, is biased by an axial force, e.g., the force resulting from the weight of the prosthesis user. If the prosthetic knee joint is flexed, the spring relaxes and causes a flexion in the hip joint and, consequently, a further flexion of the knee joint and a forward movement of the prosthetic foot. A similar mechanism is described in U.S. Pat. No. 4,051,558.

A leg prosthesis with a pneumatic energy storage unit is described in WO 01/17466 A2. Energy is stored during the extension movement in the hip joint, and the energy is released again during the subsequent flexion movement. The energy storage device comprises an electronically controlled piston/cylinder unit, the piston rod being able to telescope in order to limit the flexion of the hip joint in the swing phase. To ensure a stable and secure heel strike, a short step length is chosen.

Conventional devices for limiting the step length require manual actuation to permit substantial flexion, for example in order to sit down.

Additionally, it is not possible to achieve a truly natural gait pattern. A rapid extension of the hip joint after the heel strike is not a natural movement. The movement cannot be controlled by the patient, since it is difficult to balance on the free joint lying in front of the line of gravity. The natural lifting and swing-through of the contralateral leg during the extension of the artificial hip joint is not provided for in conventional hip joints. With a fixed step length, it is not possible to permit different walking speeds, since this requires different step lengths. In the case of a variable step length, which is dependent on the walking speed of the prosthesis user, a secure and stable heel strike must be ensured, without having to take into account the risk of a substantial and uncontrolled flexion of the hip. Damping of both the extension movement and also the flexion movement is not provided in conventional hip joints.

SUMMARY

One object of the present invention is to provide a hip joint prosthesis with which the abovementioned problems can be avoided or minimized.

The hip joint prosthesis according to one embodiment of the invention comprises connection means for securing the hip joint prosthesis to a securing device and to an artificial leg. In addition, a control unit is provided for controlling an extension movement in the hip joint and for controlling the step length. With the control unit, it is possible to control the extension movement in the stance phase and also the step length of the leg prosthesis, for example via a hydraulic control system.

In another embodiment, the control unit has at least one damper device for damping the flexion movement and/or extension movement in the hip joint, in order to control the step length and the nature of the hip flexion or hip extension. The damper device may be a hydraulic damper and comprise devices or means for adjusting the damping in the extension direction of the prosthesis and the flexion direction of the prosthesis. The control unit is may be provided with a suitable damper characteristic curve such that at an increased walking speed, with a correspondingly higher energy level, the step length is increased in a manner adapted to the natural gait pattern.

The control unit may be integrated in the hip joint to provide a compact structure, and may include adjustable valves or resistances to vary the damper characteristic curve.

For a particularly natural gait pattern, adjustment devices or means may be provided for adjusting the damping in extension and flexion. In extension, a high degree of damping is provided, which can be adjusted such that the pelvis of the patient remains virtually horizontal during roll-over on the prosthesis. A sudden extension after heel strike is avoided. This allows the patient to lift and swing through the contralateral leg during the extension of the artificial hip joint. The degree of damping can be adjusted such that a faster or slower extension is possible, depending on the individual requirements. If a high level of safety is needed, a more rapid extension can be set. If, however, a high level of comfort and a more natural gait are desired, the degree of damping chosen can be set so high that the end stop is reached just before the lifting of the prosthesis.

For the flexion movement, a first movement stage is defined by the adjustment devices or means. In the first movement stage there is no damping, or only very little damping. In a second movement stage, the damping increases, preferably progressively, up to a fixed limit value, which can be adjusted according to the prosthesis user's biometric data and his or her requirements. In a subsequent third movement stage, the damping remains constant at the end level of the second movement stage and ensures a stable heel strike without a further, uncontrolled flexion of the hip. The flexion angle, which corresponds to the length of the respective movement stage, can be adjusted such that the virtually undamped first movement stage can be prolonged or shortened depending on the individual requirements. Accordingly, the second movement stage, with the rising damper characteristic curve, can be made variable in terms of the gradient of the damper characteristic curve, for example in order to shorten the step length if a prosthesis user requires a high degree of stability. On the other hand, the respective ranges can also be chosen such that longer step lengths are permitted to meet the requirements of active prosthesis users.

In a further embodiment, the hip joint prosthesis can be provided with an energy storage unit which stores energy in the hip joint during an extension of the artificial leg and supplies at least some of this energy to the artificial leg in order to assist the flexion movement. The energy storage unit is provided in the form of spring elements, in particular plastic spring elements, steel or carbon springs, or other materials with corresponding elastic properties.

Another embodiment according to the invention is a method for controlling a hip joint prosthesis with at least one damper unit for damping the flexion movement and extension movement of an artificial leg. The damping of the extension movement such that an extension limit is not yet reached when, during a normal gait pattern, the contralateral leg is already lifted. The necessary damping of the extension movement can be adjusted so as to adapt it to the particular patient. In this way it is possible to take into account the preferences of particular prosthesis wearers and to adapt the hip joint prosthesis to the particular gait pattern. In addition, or alternatively, the control is effected such that the flexion is not damped in a first movement stage, that is to say a flexion can take place without an increased movement resistance, such that the step length on account of the flexion angle can be adjusted. During the second movement stage, the damping is increased, either linearly or progressively, after which, in a third movement stage, it is held constant at an end level which corresponds to the end level of the damping of the second movement stage.

Thus, a control of the damping in the stance phase can be carried out either in combination with the control of the damping in the swing phase or separately therefrom, in order to permit a movement adapted to the natural gait pattern.

In yet another embodiment of the invention, the flexion angle, the direction of movement, the speed of flexion of the artificial leg and/or the forces exerted on the artificial leg are measured as control parameters for the damper unit. As a function of the measured control parameters, the damping or the damping characteristic curve is then automatically adjusted to the desired extent. The control parameters are determined via sensors and are fed to an electronic evaluation unit which, on the basis of the values determined, causes an adjustment of the damper units, for example valves, via actuators.

BRIEF DESCRIPTION OF THE FIGURES

An illustrative embodiment of the invention is explained in more detail below with reference to the figures, of which.

DETAILED DESCRIPTION

Figure 1:
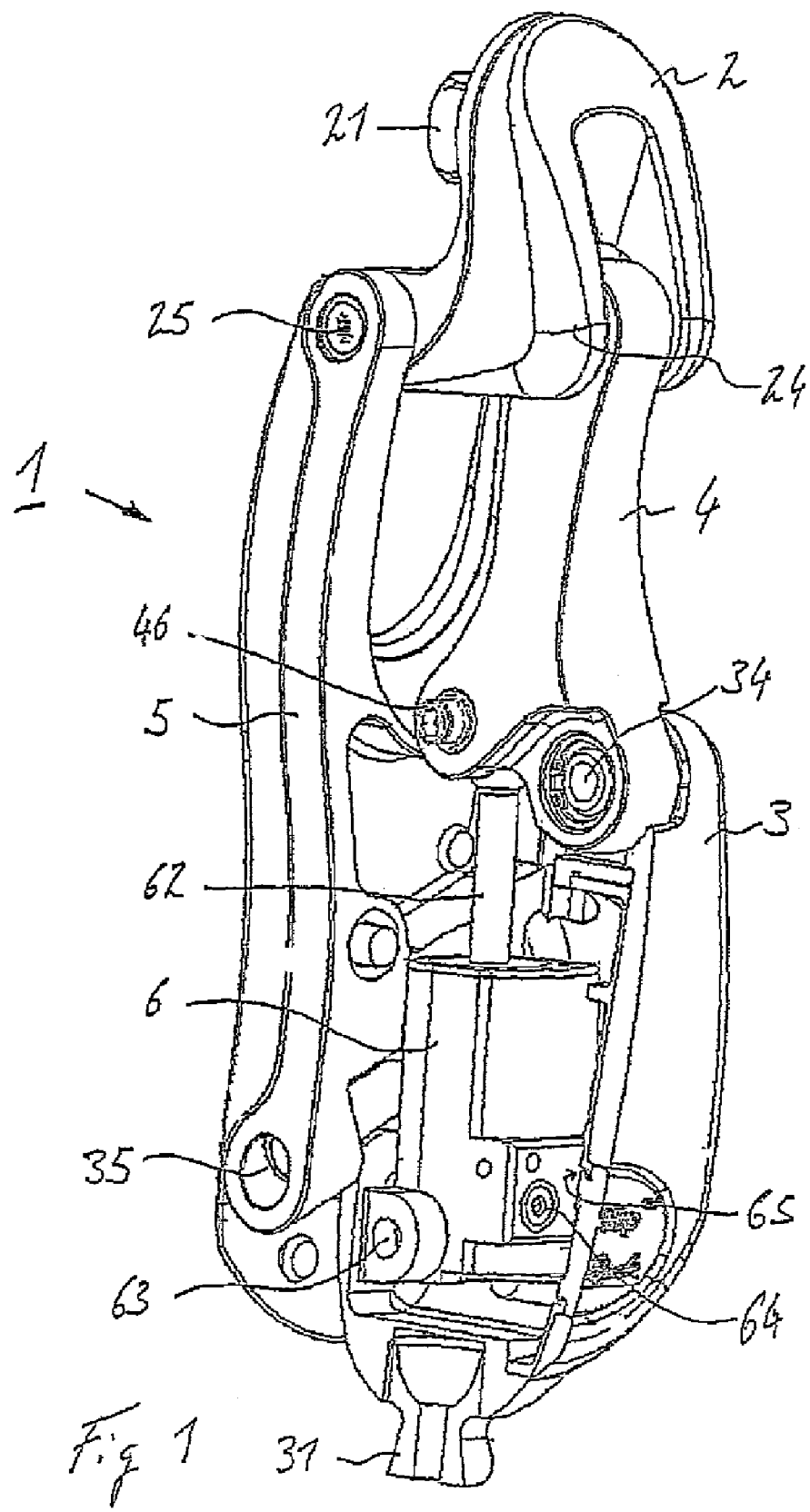
FIG. 1 shows a perspective view of a hip joint prosthesis in partial cross section.

In FIG. 1, a hip joint prosthesis 1 is shown in a perspective view and in partial cross section, with an upper part 2 and a partially cutaway lower part 3, which are connected to each other in an articulated manner via a front linking element 4 and a rear linking element 5. An upper connection piece 21 for securing to a prosthesis basket or the like is secured on the upper part 2. The upper part 2 is connected to the rear linking element 5 in an articulated manner via a rotation axle 25. The upper part 2 is connected to the front linking element 4 in an articulated manner via a spherical joint 24. The front linking element 4 is connected to a lower spherical joint 34 on the lower part 3, while the rear linking element 5 is mounted with its lower rotation axle 35 on the lower part 3.

Formed on the front linking element 4 and directed toward the interior of the joint (that is to say facing toward the rear linking element 5) is a bearing location for a piston rod 62, which is mounted pivotably about a spherical joint 46. Because of the distance between the lower spherical joint 34 and the spherical joint 46 of the piston rod 62, a pivoting of the front linking element 4 about the lower spherical joint 34 leads not only to a rotation relative to the piston rod 62, but also to a displacement of the piston rod 62 such that it is moved to and fro as a function of the direction of rotation of the front linking element 4.

The piston rod 62 protrudes into the lower part 3 and is received there by a control unit 6, which is mounted rotatably about the rotation axle 63 in the lower part 3. A lower connection piece 31 for connection to an artificial leg is secured on the bottom end of the lower part 3.

In the lower part 3, the control unit 6 is held so as to be movable about a swivel axle 63. The swivel axle 63 of the control unit 6 lies at the lower end of the control unit 6 and prevents jamming of a piston which is guided on the piston rod 62 inside the control unit 6. Jamming would occur in the case of a rigid mounting of the control unit 6 because of a second movement component perpendicular to the orientation of the piston rod 62. This second movement component arises from the swivel movement about the lower spherical joint 34 of the front linking element 4 and the resulting movement of the swivel axle 46 of the piston rod 62 about a portion of a circle.

Figure 2:
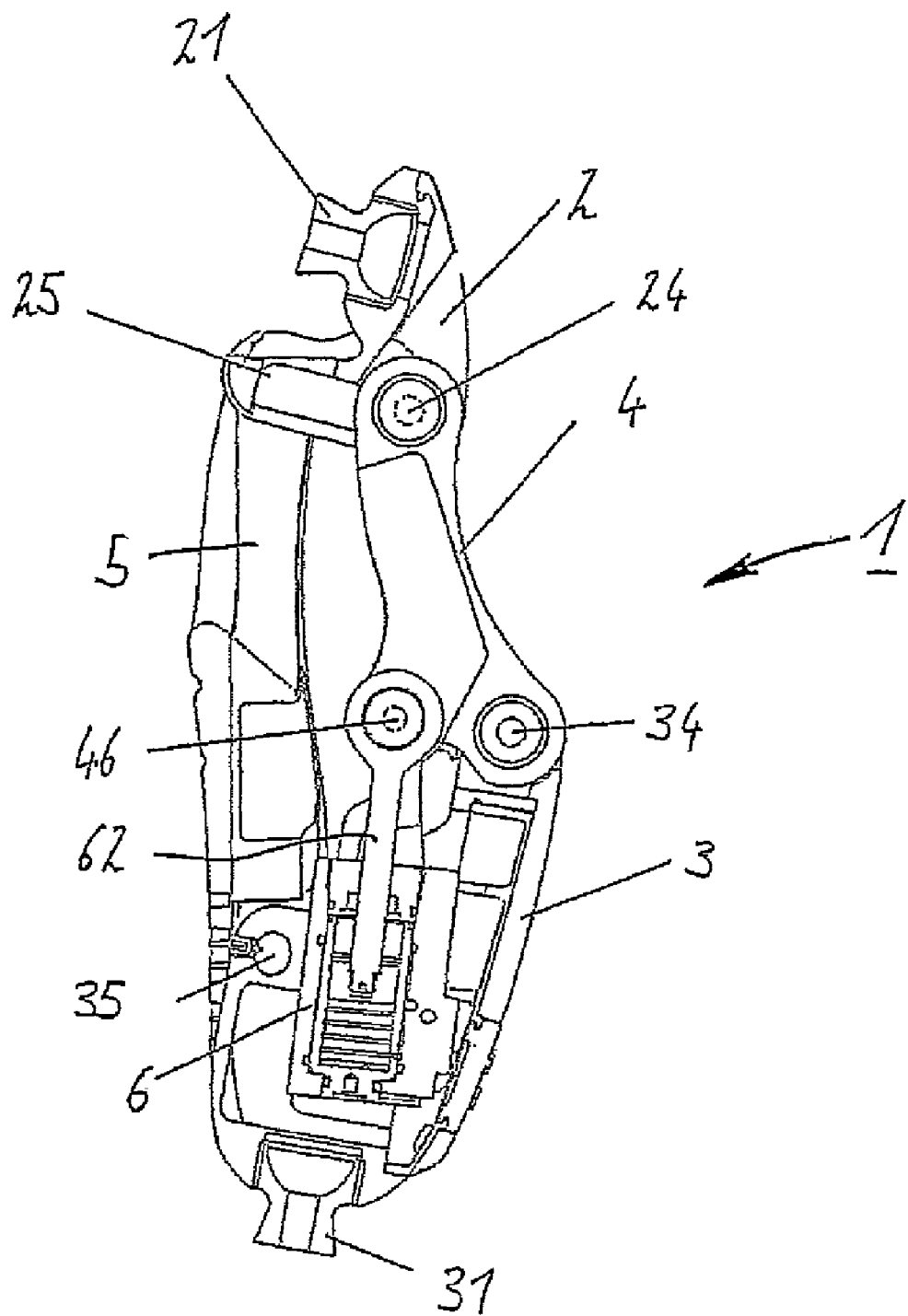
FIG. 2 shows a cross-sectional view of a hip joint prosthesis in slight flexion.

FIG. 2 shows a cross-sectional overall view of the hip joint prosthesis 1.

Figure 3:
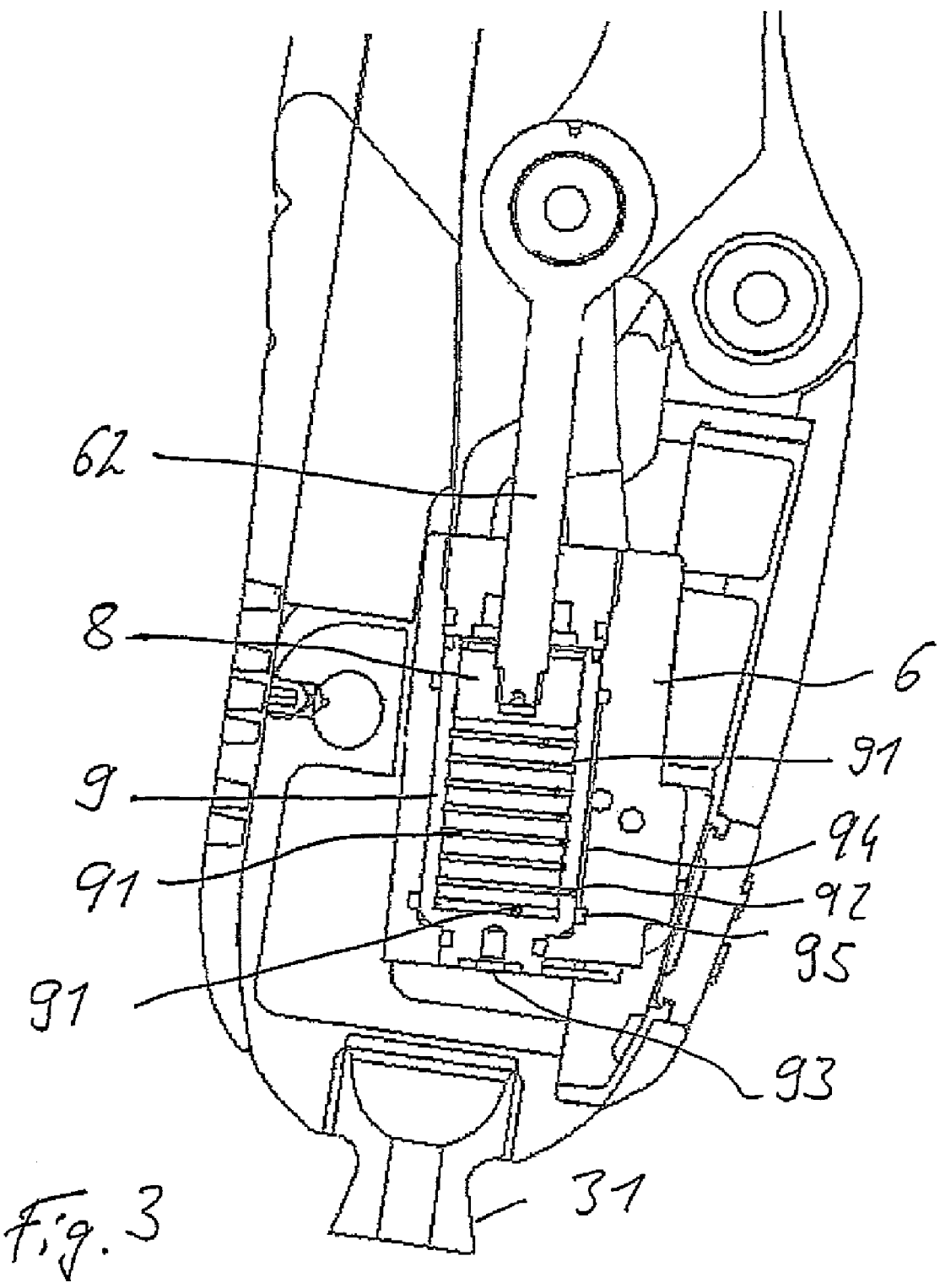
FIG. 3 shows a detail of FIG. 2.

In FIG. 3, the lower part 3 of hip joint prosthesis 1 is shown in an enlarged detail, in a slightly flexed position in which the piston 8 is arranged at the upper end of the cylinder space formed by the cylinder wall 9.

Bores 92 are arranged in grooves 91, and are mutually offset in the circumferential direction and can each be brought into alignment with a return channel 94. The lowermost groove 91 is permanently connected to an annular channel 95, which forms the minimal hydraulic return flow to maintain damping constant at an end level. Prior to reaching the groove 91 that communicates with the return channel 94 via a bore 92, a correspondingly reduced damping level is provided by a higher return flow quantity of the hydraulic fluid flowing through the two bores 92. If the piston 8 reaches the bore 92 that communicates with the return channel 94, this bore is closed resulting in a rising damping characteristic curve for this second area. By means of this adjustable damping in the control unit 6, it is possible to control the extension movement in the hip joint. By virtue of the provision of a spring element 7 and the adjustability of the damping in the flexion movement, it is possible to adjust the step length.

The control unit 6 is a separately formed, pivotably mounted hydraulic damper unit integrated in the lower part 3 of the hip joint 1. An alternative arrangement of the control unit or damper unit 6 at another location of the hip joint 1 is likewise possible. Because valves 64, 65 can be accessed from the outside, the respective damper characteristic curves and the movement stages can be adjusted individually. This also arises in particular from the adjustability of the arrangement of the bores 92.

The mode of operation of the control unit 6 will be explained with reference to the enlarged view in FIG. 3. The piston 8 is secured at the lower end of the piston rod 62. Within the control unit 6, the cylinder inner wall 9 is mounted rotatably and includes grooves 91. Each groove 91 has an associated opening 92 which can be rotated by rotation of the cylinder wall 9 using a tool that engages a recess 93 at the lower end, for example in a slit or a hexagon socket, until the bore 92 is flush with a vertically aligned return channel 94. Rotation of the cylinder wall 9 determines which bore 92 is flush with the return channel 94 and opened and, therefore, to which groove 91 the piston 8 can move freely in flexion. If the hip joint prosthesis 1 is flexed, the piston rod 62 moves downward, and, if the hip joint is extended, the piston 8 moves correspondingly upward. The recess 93 is accessible from outside via an access opening, such that it is possible to adjust the flexion angle as a function of the position of the cylinder wall 9 and of the respectively flush bore 92 with the return channel 94.

A groove can be cut into the piston 8 to cause a progressive increase in damping after the respective groove 91 in the cylinder wall is reached. After the piston groove has been driven completely in front of the cylinder wall groove 91, a high degree of damping becomes active, which can be adjusted with an extension valve 64.

The extension is reduced with a constant or slightly increasing damping. The damping can be adjusted with the second valve 65 on the hydraulics.

The control unit 6 is thus designed as a hydraulic damper which has a progressive damper characteristic curve and can damp both the flexion movement and also the extension movement in the hip joint and can mechanically control the flexion angle and the extension movement via valves 64, 65. Until the bore 92 is flush with the return channel 94, there is no or only minimal damping, whereas the damping increases from the time the piston 8 reaches the cylinder wall groove 91. After the bore has been reached and completely closed off, there is a high degree of damping through the bore 92 in the last groove 91, which remains constant until the end of the flexion movement. In extension, the oil flows through an upper bore 92 (not shown in this figure) into the upper groove 91, the damping characteristic curve being able to be adjusted via the valve 65 or a throttle.

Figure 4:
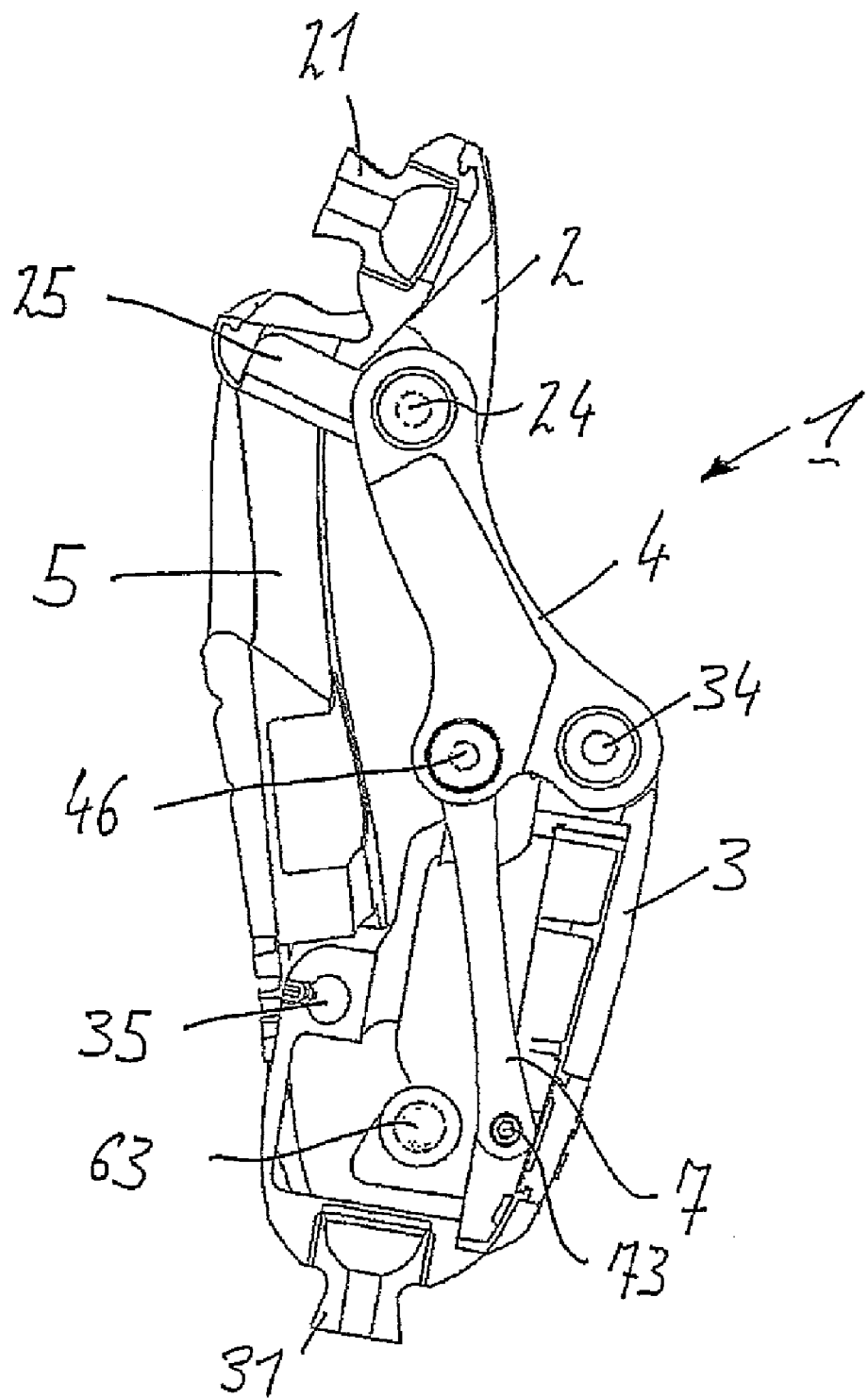
FIG. 4 shows a side view of a hipjoint prosthesis in a flexed position.

FIG. 4 shows the hip joint prosthesis 1 in a flexed position. The spherical joint 46 of the piston rod 62 also constitutes an attachment point for the spring element 7, which is arranged with its lower end on a swivel axle 73 on the lower part 3. In the flexed position of the hip joint prosthesis 1, the spring element 7, which can be designed in particular as a plastic spring or another elastic band, is barely extended since all the energy that was stored in the spring element 7 in the extension position has been transferred to the lower part 3 and thus to the artificial leg (not shown). The spring element 7 supports the flexion movement of the hip joint prosthesis 1 by placing a downward force on the spherical joint 46 of the piston rod 62, which is secured on the front linking element 4, and by moving it in the direction of the lower part 3.

Figure 5:
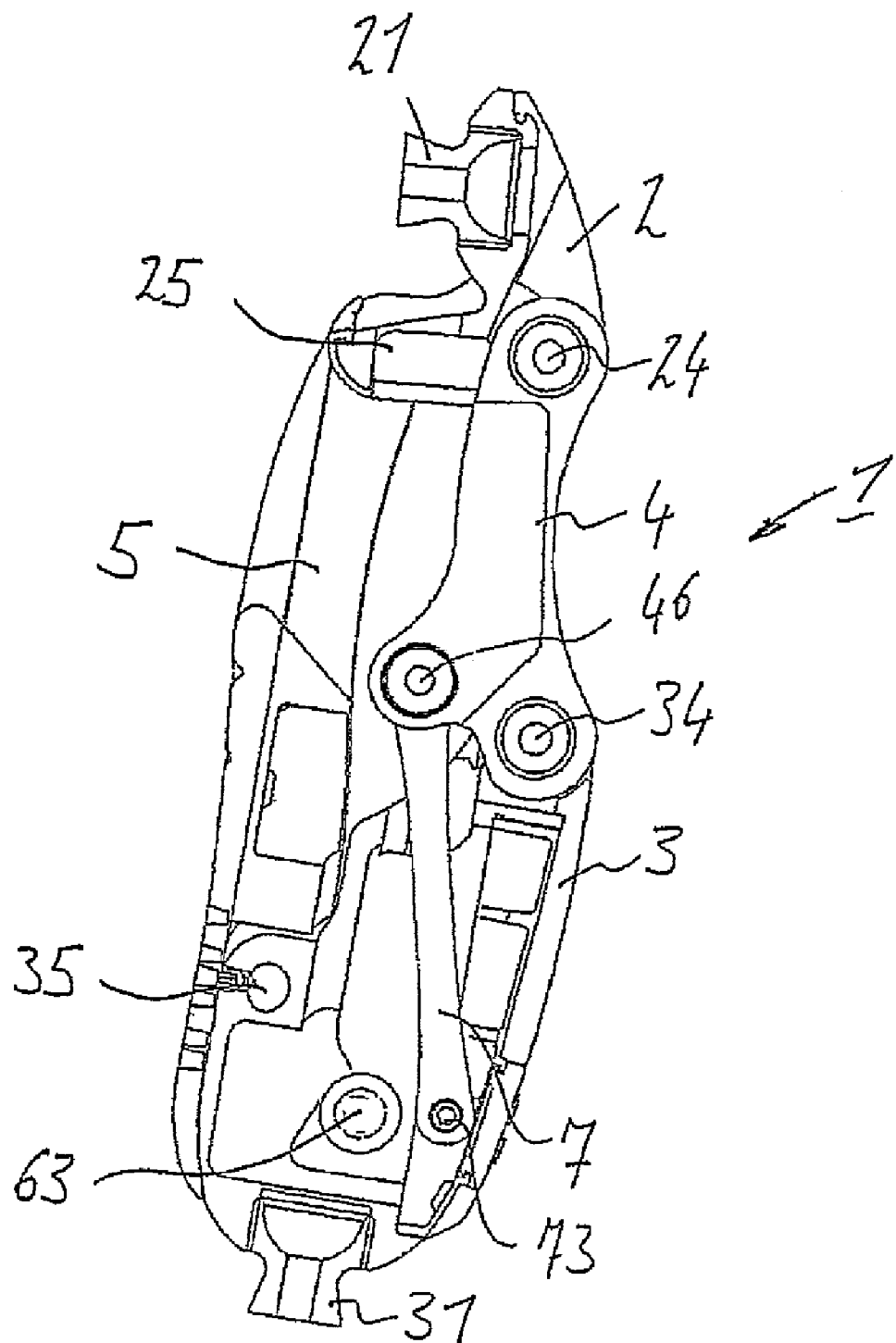
FIG. 5 shows a hip joint prosthesis in an extended position.

The extension position of the hipjoint prosthesis is shown in FIG. 5, which corresponds in position to that of FIG. 1. The spring element 7 is at maximum extension and has a high energy content since the upper attachment point 46 on the front linking element 4 is located at a maximum distance from the lower swivel axle 73 of the spring element 7. Upon extension of the artificial leg, the expended energy is stored in the spring unit 7, which can also be designed as a conventional tension spring, and, upon the flexion movement at least some energy is supplied to the artificial leg.

In principle, the control unit 6 or damper unit can be mounted at a location on the hip joint prosthesis 1 other than that shown, and also on other embodiments of hip joint prostheses, for example on a monoaxial hip joint. Likewise, the mode of operation of the control unit can be reversed, if appropriate, such that the piston moves outward during a flexion movement and inward during an extension movement.

FIGS. 6 to 9 are schematic representations of the damper device with the piston rod 62, the piston 8, the hydraulic cylinder 9, the adjustable flexion valve 64 and the adjustable extension valve 65. The adjustable valves 64, 65 act as throttles via which damping of the hip joint can be adjusted. The grooves 91 in the hydraulic cylinder 9 are not shown. The lower bore 92 constitutes the connection to the return channel 94. A double arrow assigned to the bore 92 indicates the vertical adjustability and, consequently, the adjustability of the flexion angle without operation of the flexion valve 64.

Figure 6:
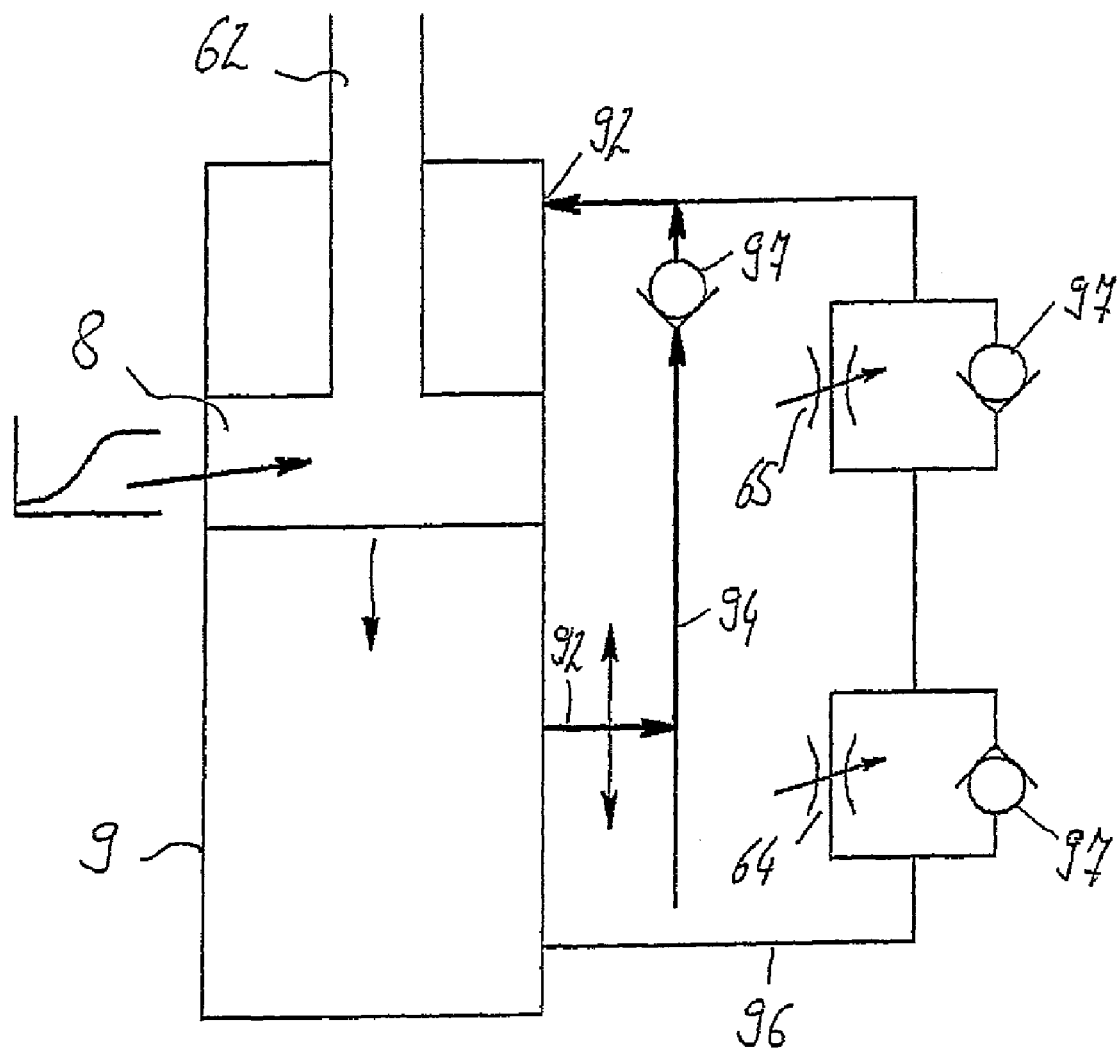
FIGS. 6 to 9 show circuit diagrams of various hip joint hydraulics.

In FIG. 6, the piston 8 is moved downward as a result of a flexion movement of the artificial leg. The hydraulic fluid thus flows without great resistance through the vertically adjustable bore 92 via which the step lengths can be adjusted, through an upper, vertically fixed upper bore 92 back into the upper part of the cylinder 9. A check valve 97 can be arranged in the return channel 94, which check valve 97 allows the hydraulic fluid to flow into the upper part during a flexion movement but prevents it from flowing back during an extension movement.

Figure 7:
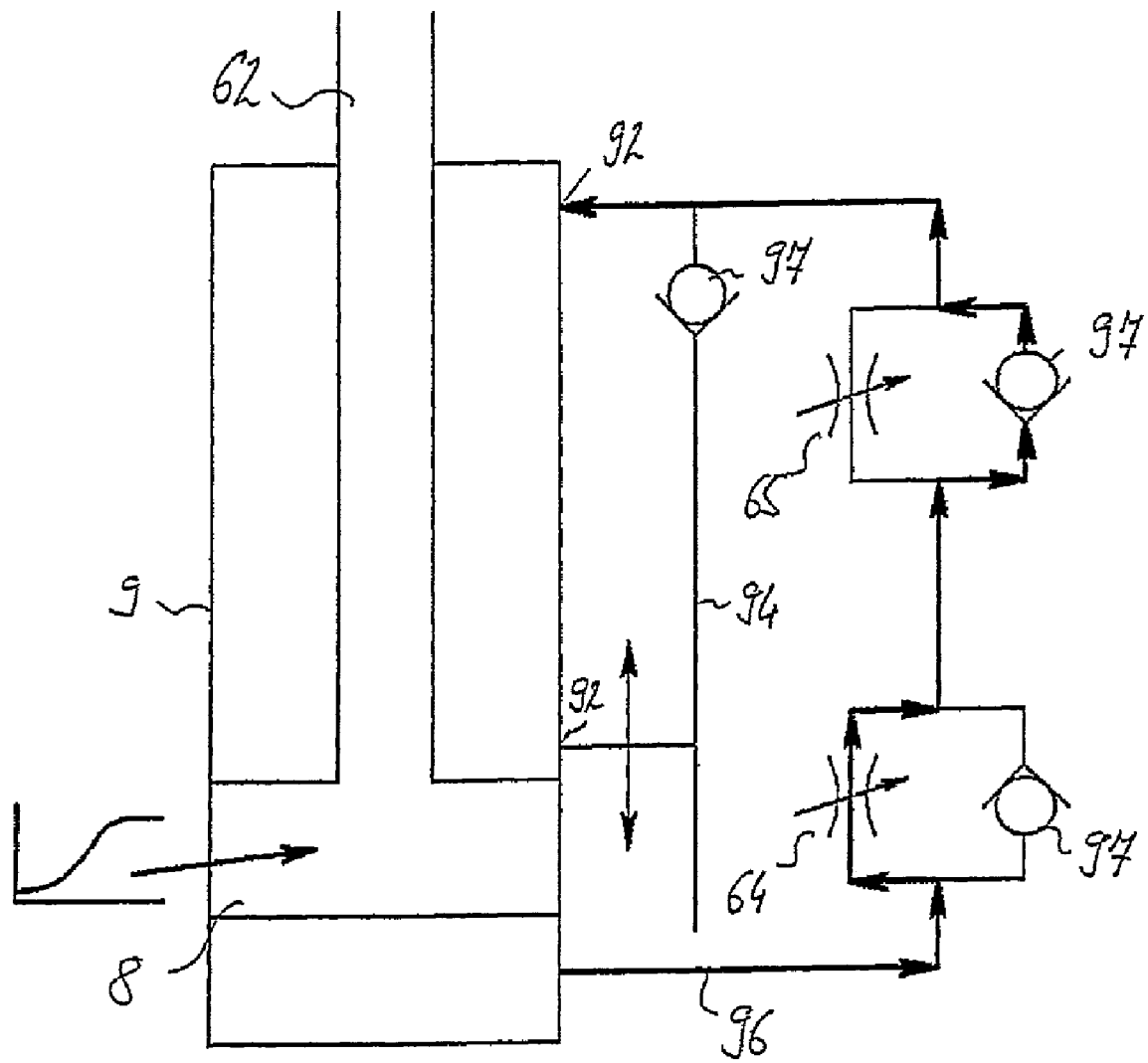

FIG. 7 shows the state in which the piston 8 has reached and moved past the lower bore 92. After the lower bore 92 has been reached, the hydraulic fluid flows to the valves 64, 65 via connection channel 96 separate from the return flow channel 94. Before the lower bore 92 was reached and closed off by the piston 8, the higher flow resistance in the connection channel 96 and the valves 64, 65, 97 located therein meant that very little hydraulic fluid, if any, flowed. After closure of the vertically adjustable bore 92, the hydraulic fluid is conveyed exclusively through the connection channel 96. The damper force is increased by the flexion valve 64, which damps the flexion of the hip joint, such that the damping characteristic curve rises. There is no flow through the extension valve 65, since a bypass with a check valve 97 with lower flow resistance is connected in parallel.

Figure 8:
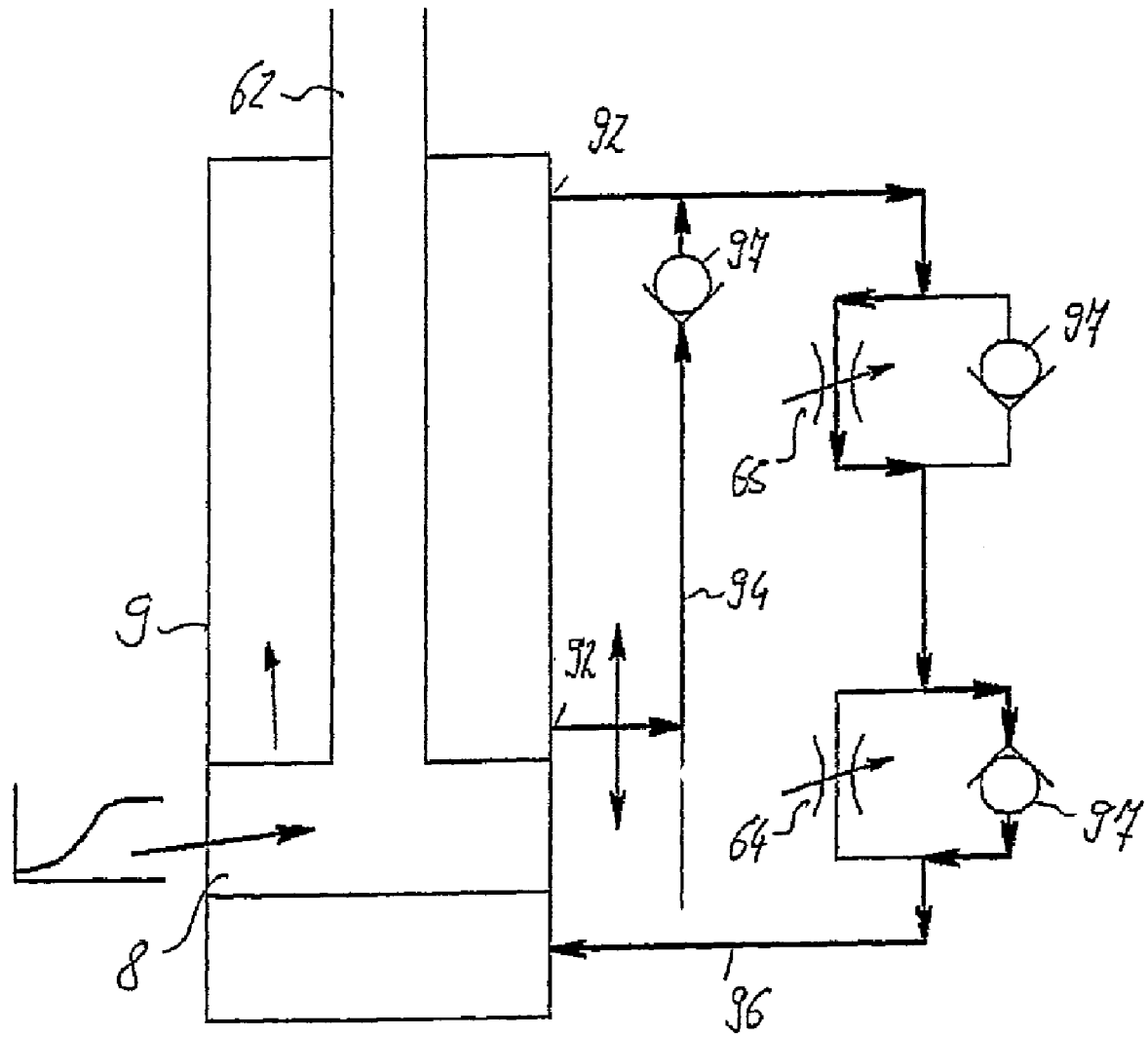
Figure 9:
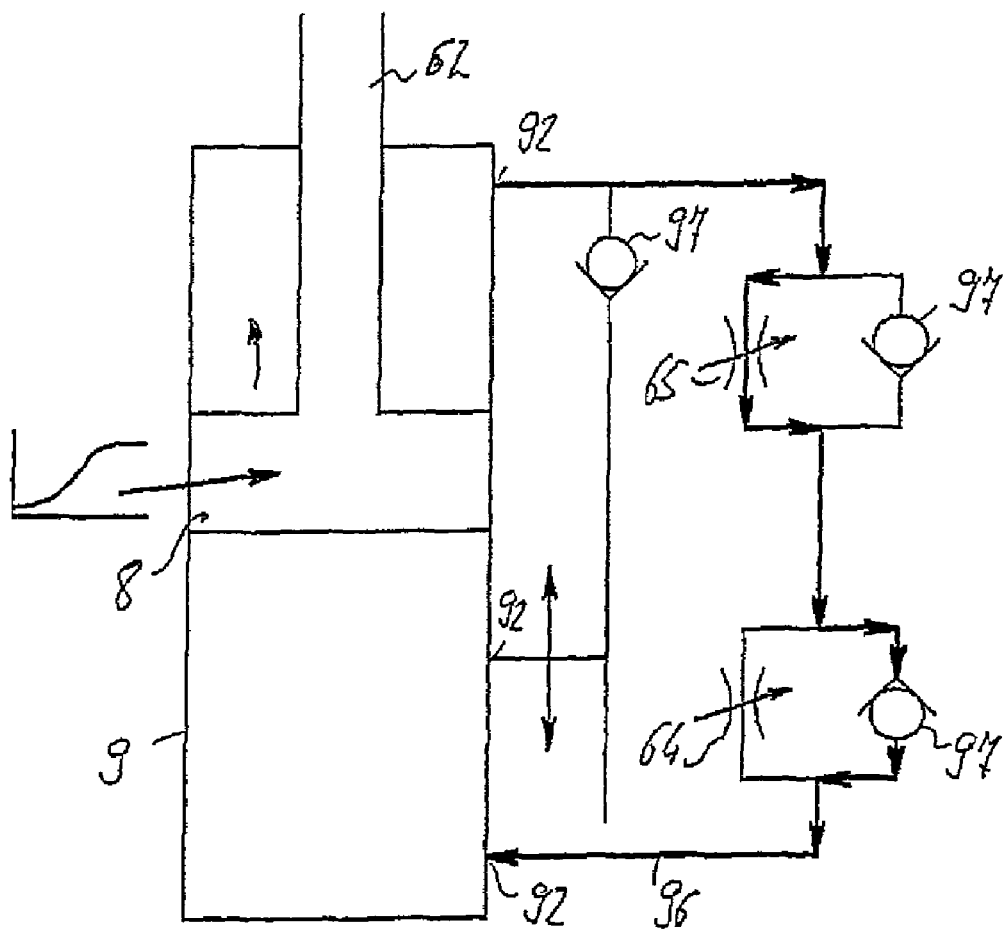

If extension is initiated, the piston 8 moves upward, as is shown in FIG. 8. The extension movement is then damped via the extension valve 65, irrespective of whether the hydraulic fluid flows through the upper or lower bore 92. The direction of flow of the hydraulic fluid is indicated by the arrows. The check valve 97 in the return flow channel 94 ensures that all of the hydraulic fluid flows through the extension valve 65. The flexion valve 64 has a bypass with a check valve 97 and has no influence on the damping characteristic curve in the extension movement.

Figure 10:
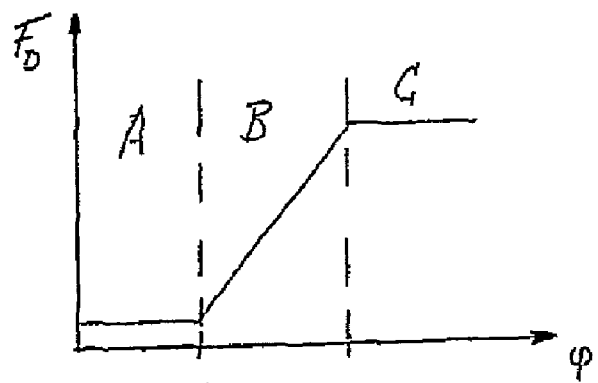
FIG. 10 shows a diagram of damping forces for control of the swing phase.

FIG. 10 is a damper force diagram over the angle $\phi$ in which the different damping phases and effective forces during flexion are shown. In a first movement stage A, the damper force $F_D$ is negligible and is composed of the damping factors inherent to the system, for example frictional resistances on bearings, or a permanently present flow resistance of the hydraulic fluid. A desired damping does not take place in movement stage A. In a second movement stage B, the damping and thus also the damper force being overcome is increased, in the example shown linearly increased, specifically to an end level which is reached and maintained in the third movement stage C. Such a damper force curve can be realized by switching on corresponding damper elements or flow resistances. If the hip joint is extended upon completion of the flexion movement, the damping of the extension movement can be adjusted such that the maximum extension or an extension limit is not reached when, during a normal gait pattern such as normal walking speed, the contralateral leg is already lifted.

The invention claimed is:

1. A hip joint prosthesis comprising:
   connection means for securing the hip prosthesis to an upper securing device and to an artificial leg; and
   a control unit for controlling an extension movement in the hip joint and for controlling a step length of the artificial leg;
   wherein the control unit includes at least one damper device for damping a flexion movement and the extension movement in the hip joint;
   wherein during the flexion movement the damper device is adapted to avoid damping in a first movement stage, to apply increasing damping during a second movement stage, and to maintain constant damping from an end level of the second movement stage through a third movement stage.

2. The hip joint prosthesis as claimed in claim 1, wherein the control unit includes a hydraulic damper.

3. The hip joint prosthesis as claimed in claim 1, wherein the control unit employs a progressive damper characteristic curve to control the flexion movement.

4. The hip joint prosthesis as claimed in claim 1, wherein the control unit is integrated in the hip joint.

5. The hip joint prosthesis as claimed in claim 1, wherein the control unit includes adjustable valves for varying a damper characteristic curve to control the flexion movement.

6. The hip joint prosthesis as claimed in claim 1, wherein the damper device maintains constant damping during extension.

7. The hip joint prosthesis as claimed in claim 1, further comprising an energy storage unit which stores energy in the hip joint during an extension of the artificial leg and supplies at least some stored energy to the artificial leg during a flexion of the artificial leg.

8. The hip joint prosthesis as claimed in claim 7, wherein the energy storage unit includes spring elements.

9. A method for controlling a hip joint prosthesis including at least one damper unit for damping a flexion movement and an extension movement of an artificial leg during a normal gait pattern with a contralateral leg, the method comprising:
   extending the artificial leg;
   applying damping to the extension of the artificial leg such that an extension limit is not reached when the contralateral leg is lifted;
   flexing the artificial leg through a first, second and third movement stage;
   avoiding damping to the flexion of the artificial leg through the first movement stage;
   applying an increasing damping to the flexion of the artificial leg in the second movement stage; and
   maintaining a constant damping to the flexion of the artificial leg from an end of the second movement stage through the third movement stage.

10. The method of claim 9, further comprising the steps of:
    measuring at least one of a flexion angle of, a direction of movement of, a movement speed of and a force exerted upon the artificial leg; and
    adjusting the damping of the flexion or extension based on the measurement.

11. A hip joint prosthesis comprising:
    a connection device configured to secure the hip prosthesis to an upper securing device and to an artificial leg; and
    a control unit including at least one damper device configured to dampen a flexion movement and the extension movement in a hip joint;
    wherein during the flexion movement the damper device is adapted to avoid damping in a first movement stage, to apply increasing damping during a second movement stage, and to maintain constant damping from an end of the second movement stage through a third movement stage.

12. The hip joint prosthesis as claimed in claim 11, wherein the control unit includes a hydraulic damper.

13. The hip joint prosthesis as claimed in claim 11, wherein the control unit employs a progressive damper characteristic curve to control the flexion movement.

14. The hip joint prosthesis as claimed in claim 11, wherein the control unit is integrated in the hip joint.

15. The hip joint prosthesis as claimed in claim 11, wherein the control unit includes adjustable valves for varying a damper characteristic curve to control the flexion movement.

16. The hip joint prosthesis as claimed in claim 11, wherein the damper device maintains constant damping during extension.

17. The hip joint prosthesis as claimed in claim 11, further comprising an energy storage unit which stores energy in the hip joint during an extension of the artificial leg and supplies at least some stored energy to the artificial leg during a flexion of the artificial leg.

18. The hip joint prosthesis as claimed in claim 17, wherein the energy storage unit includes spring elements.

* * * * *